US009082268B2

(12) United States Patent
De Geest et al.

(10) Patent No.: US 9,082,268 B2
(45) Date of Patent: Jul. 14, 2015

(54) COMMUNICATION UNIT FOR A PERSON'S SKIN

(75) Inventors: Jan De Geest, Zwijndrecht (BE); Wim De Geest, La Hulpe (BE)

(73) Assignee: THERASOLVE NV, Diepenbeek (BE)

( * ) Notice: Subject to any disclaimer, the term of this patent is extended or adjusted under 35 U.S.C. 154(b) by 349 days.

(21) Appl. No.: 11/597,730

(22) PCT Filed: May 26, 2005

(86) PCT No.: PCT/EP2005/052411
§ 371 (c)(1), (2), (4) Date: May 23, 2007

(87) PCT Pub. No.: WO2005/119610
PCT Pub. Date: Dec. 15, 2005

(65) Prior Publication Data

US 2008/0021519 A1 Jan. 24, 2008

(30) Foreign Application Priority Data

May 28, 2004 (EP) .................................... 04102382
Dec. 27, 2004 (EP) .................................... 04107002

(51) Int. Cl.
*A61N 1/04* (2006.01)
*G08B 6/00* (2006.01)
*G08B 21/24* (2006.01)

(52) U.S. Cl.
CPC . *G08B 6/00* (2013.01); *G08B 21/24* (2013.01)

(58) Field of Classification Search
USPC ............. 607/2, 115, 148, 149, 152, 139, 140, 607/142, 144; 455/575.6, 567; 340/309.7
See application file for complete search history.

(56) References Cited

U.S. PATENT DOCUMENTS

| | | | | |
|---|---|---|---|---|
| 3,562,408 A * | 2/1971 | Collins et al. | 348/62 |
| 4,708,716 A * | 11/1987 | Sibalis | 604/20 |
| 5,554,967 A * | 9/1996 | Cook et al. | 340/309.7 |
| 5,643,332 A * | 7/1997 | Stein | 607/49 |
| 5,686,882 A | 11/1997 | Giani | |
| 5,755,747 A * | 5/1998 | Daly et al. | 607/55 |
| 5,894,271 A * | 4/1999 | Namisniak | 340/407.2 |
| 5,991,655 A * | 11/1999 | Gross et al. | 604/20 |
| 6,032,058 A | 2/2000 | Higuchi et al. | |

(Continued)

FOREIGN PATENT DOCUMENTS

| | | |
|---|---|---|
| CN | 1187140 A | 7/1998 |
| GB | 2 386 207 | 9/2003 |

(Continued)

OTHER PUBLICATIONS

Office Action dated Oct. 1, 2013 for Application No. JP 2012-052019.

(Continued)

*Primary Examiner* — Carl H. Layno
*Assistant Examiner* — Erica Lee
(74) *Attorney, Agent, or Firm* — Ladas & Parry LLP

(57) ABSTRACT

An electric communication unit to be placed on a person's skin. The electric communication unit includes a support element, a series of body contacts, and a pulse generator. The pulse generator generates a series of pulses and transmits the series of pulses to the series of body contacts, the series of body contacts being provided to transmit the series of pulses onto the skin of the person. The electric communication unit is in the form of a patch.

27 Claims, 10 Drawing Sheets

(56) References Cited

U.S. PATENT DOCUMENTS

| | | | |
|---|---|---|---|
| 6,171,294 | B1 | 1/2001 | Southam et al. |
| 6,175,763 | B1 * | 1/2001 | Sorenson et al. ............... 604/20 |
| 6,272,379 | B1 * | 8/2001 | Fischell et al. .................... 607/5 |
| 6,282,448 | B1 * | 8/2001 | Katz et al. ....................... 607/48 |
| 6,353,396 | B1 * | 3/2002 | Atlas .......................... 340/693.9 |
| 6,546,285 | B1 * | 4/2003 | Owen et al. ....................... 607/5 |
| 6,584,352 | B2 * | 6/2003 | Combs et al. ..................... 607/9 |
| 2001/0029194 | A1 * | 10/2001 | Ketola et al. .................. 455/567 |
| 2002/0143373 | A1 * | 10/2002 | Courtnage et al. .............. 607/91 |
| 2003/0083559 | A1 * | 5/2003 | Thompson .................... 600/372 |
| 2003/0199945 | A1 * | 10/2003 | Ciulla ............................ 607/48 |
| 2004/0034289 | A1 * | 2/2004 | Teller et al. ................... 600/300 |
| 2004/0039328 | A1 * | 2/2004 | Henley ............................ 604/20 |
| 2004/0073095 | A1 * | 4/2004 | Causey et al. ................. 600/300 |
| 2004/0192423 | A1 * | 9/2004 | Nevermann ................ 455/575.6 |
| 2005/0245970 | A1 * | 11/2005 | Erickson et al. .................. 607/2 |
| 2006/0084480 | A1 * | 4/2006 | Patino et al. .................. 455/567 |

FOREIGN PATENT DOCUMENTS

| | | | |
|---|---|---|---|
| JP | 3198871 | A | 8/1991 |
| JP | 3030413 | U | 8/1996 |
| JP | 9331577 | A | 12/1997 |
| JP | 11-511056 | A | 9/1999 |
| WO | 96/02046 | A1 | 1/1996 |
| WO | 97/37583 | A1 | 10/1997 |
| WO | 00/15120 | A1 | 3/2000 |
| WO | 03/028797 | A1 | 4/2003 |

OTHER PUBLICATIONS espacenet English abstract of DE 196 14 255 C1 dated Sep. 10, 2013.

Office Action dated Jun. 13, 2008 for Application No. CN 200580017396.X, with English version.

Office Action dated May 22, 2012 for JP Application No. 513936/20007, with English version.

"Research of transdermal drug delivery by electroporation", *Chinese Pharm J*, 1998, March, vol. 33, No. 3, pp. 129-132.

espacenet abstract of CN 1187140A.

espacenet abstract of JP 9331577 A.

espacenet abstract of JP 3198871A.

Decision to Grant for JP Application No. 513936/2007.

* cited by examiner

Memory map

| | Data | |
|---|---|---|
| Address | D0 D1 D2 D3 D4 D5 D6 D7 D8 D9 D10 D11 D12 D13 D14 D15 | |
| 0 | Identifier | |
| 1 | Strength of current | |
| 2 | Pulse length | |
| 3 | Pulse duty cycle | |
| 4 | Burst length | |
| 5 | Burst duty cycle | |
| 125 | Activation length | |
| 126 | Time of antenna inactivity | |
| 127 | Clock correction | |
| 128 | Time of activation1 | C 1 |
| 129 | Time of activation 2 | C 2 |
| 130 | Time of activation 3 | C 3 |
| 250 | Time of activation 123 | C 123 |
| 251 | Time of activation 124 | C 124 |
| 252 | Time of activation 125 | C 125 |
| 253 | Time of activation 126 | C 126 |
| 254 | Time of activation 127 | C 127 |
| 255 | Time of activation 128 | C 128 |

*Fig. 10*

COMMUNICATION UNIT FOR A PERSON'S SKIN

FIELD OF THE INVENTION

The invention relates to an electric communication unit provided to be placed on a person's skin, said unit comprising:

- a support element comprising:
  - a series of body contacts,
  - a pulse generator connected to the series of body contacts, and provided for generating a series of pulses upon receipt of a first signal and for transmitting the series of pulses to said series of body contacts, said series of body contacts being provided to transmit said series of pulses onto the skin of said person, and
- a power supply connected to the pulse generator.

BACKGROUND OF THE INVENTION

The continuous need for new and better medical treatments results in the performing medication of today. Economic and social importance constantly push the pharmaceutical sector to create the most effective medicine possible. The following factors represent main influence in the final effect of a treatment:

1. The characteristics of the medicine per dose. Clinical trials are executed to study and determine the most adequate molecules and their necessary concentrations to cure the patient properly.
2. The timely administration of the medicine (with a frequency recommended by the manufacturer, the pharmacist or on doctor's orders) which is strongly depending on the patient's adherence.

Recent studies made by order of the World Health Organization show the importance of the second factor, namely the patient's compliance. Half of the actual administered medicine does not lead up to an effective treatment due to lack of adherence, despite the good intrinsic quality of the medicine. It is clear that this problem has an enormous impact worldwide both on social and on economic level.

These studies conclude that there is an urgent need for a modern solution to this problem. The present invention offers an answer based on a new concept.

Up to date, there exists some electric communication devices which solve partially the problem of the compliance of the patient.

For example, U.S. Pat. No. 4,708,716 discloses an applicator for a transdermal drug delivery medication comprising an electric circuitry which is closed by the skin when the applicator is applied to the skin. This application causes the current to flow and the medicament to move through the skin into the blood stream. An electrode may be employed in a loop circuit to feedback a signal when a desired dosage level is achieved in the blood stream, so that with such feedback loop, a demand type applicator is achieved which regulates the drug dosage as desired. An LCD or an electrochemical phototropic material (ECM) may be incorporated in the circuitry of the device to serve as an indicator. With completion of the circuit, the indicator is activated so as to provide a positive indication that the drug is being delivered transdermally.

Unfortunately, such a device is restricted to transdermal drugs and is difficult to manufacture. Indeed, the operating of the device is associated with the transfer through the skin of a liquid medicine which will migrate to the skin from the drug reservoir upon the effect of the current flow. Therefore, the system requires the construction of a drug reservoir, having electrodes to force the drug to migrate and the construction of an electric circuitry which will be closed by the skin. Therefore, if a small portion is not well applied onto the skin, the closing of the circuitry will not occur and the device will not operate properly.

Moreover, the device according to U.S. Pat. No. 4,708,716 confirms the patient that the diffusion of the drug has correctly occurred with a transmission of a luminous signal which can cause troubles in some environments like hospital surrounding or the like. Such a luminous signal is not perceptible when the wearer of the device is sleeping. Therefore, it can happen that the medicine is not correctly taken by the patient, for example during the night or when busy with a task asking concentration. By providing a confirmation with a positive indication that the drug is being delivered transdermally, the device does not inform the patient of a dysfunction and the patient should be attentive to check if the signal has been emitted by the device.

Further the device according to U.S. Pat. No. 4,708,716 is only usable on the patient himself or herself.

Another example is given in U.S. Pat. No. 6,175,763. The electrotransport system according to U.S. Pat. No. 6,175,763 comprises a drug reservoir for delivering drug upon the effect of a electrotransport drive current through the skin. The electrotransport system comprises a sensor for sensing a condition or an event associated with the operation of the system, a controller and a tactile signal generator for generating a tactile signal which can be sensed. In particular, the sensor is a pH sensor which senses the pH of the drug in the reservoir or a sensor which senses the drug content in the reservoir. If a problem occurs in the device, such an abnormal pH or an abnormal content in the reservoir, for example an empty reservoir, the controller which is provided to receive the signal from the sensor and to control the tactile signal generator, detects an abnormal value and a tactile signal is transmitted to the skin of the patient.

Such a device resolves partially the problems of the device of the U.S. Pat. No. 4,708,716 by providing a tactile signal which can be sensed when the patient is sleeping or busy. The tactile signal is only transmitted to the patient's skin when a problem occurs and no signal will be transmitted when the device has correctly operated.

Unfortunately, such a device is also only applicable in a transdermal drug application, as the operating is associated with the migration of the drug from the reservoir. The tactile signal is also associated with the functioning, in particular with a dysfunctioning of the device. The device is also difficult to manufacture as it is required the presence of a drug reservoir comprising a liquid drug and captors, like level captor or pH captor and an electric circuitry.

The electric circuitry is also closed by the skin of the wearer and if the device is not well applied, the device will not correctly function and a tactile signal shall be generated. Moreover, the device according to U.S. Pat. No. 6,175,763 is only usable on the patient himself or herself.

Indeed, the devices according to both US patents should be manufactured with the drug contained in a reservoir and should comprise an electronic or electric circuitry. Therefore, the manufacturing steps are not easy and the resulting device is expensive. Moreover, such device can alert the patient about a dysfunction of the device but does not solve the problem of the timely administration of the medicine for example a tablet medicine or a pill medicine or even an injection medicine (with a frequency recommended by the manufacturer, the pharmacist or on doctor's orders) which is strongly depending on the patient's adherence.

Another kind of electric communication device exists. For example, the electric communication device described in the GB 2 386 207. The device of GB 2 386 207 is disclosed in the preamble of claim 1. It is a silent anatomic alarm system comprising an emitter wireless base unit and an anatomic wireless unit (electric communication unit). The anatomic wireless unit is able to output an electric current onto the skin of the user on receipt of a signal transmitted from the base unit. Such an electric communication system is, for example provided to remind the patient that he or she has to take his or her pill, tablet, etc. or to make his or her injection. This device consists of two rings connected together, and provided to be respectively fastened, for example on a user's foot and on the user's ankle. This device can find a utility in medication that were not transdermally applied, such as tablets, pills, etc. and can be applied to another person than the patient, but this device is bulky and not operable outside the transmission range from the base unit.

Therefore, known electric communication units have thus important limitations at several levels: too large, poor user-friendlyness, not easy to manufacture, no possibility to alert independently of the user's conditions, poor discretion, only applicable for specific types of medicine, not conceived for easy addition to existing medicament packaging and the like.

It is an object of the invention to palliate at least some of these drawbacks by providing a broad applicable concept which improves reliability by alerting the patient that he or she has to take his or her medicine and which can be applied on the skin of another person while being independent of the user conditions.

SUMMARY OF THE INVENTION

To this end, the invention provides a unit according to the preamble of claim 1, characterised in that the electric communication unit is in the form of a patch provided to be placed onto the person's skin and in that the pulse generator further comprises a processing unit with a memory, said processing unit being provided:

- to store a second signal, said second signal comprising data indicative at which time said first signal should be generated, and
- to generate and transmit said first signal to said pulse generator.

The electric communication unit according to the invention is more easy to manufacture because of its planar shape, is small, user-friendly, not bulky, discrete, etc. Moreover the unit is very easy to place because of the patch concept. In addition, by being in permanent contact with the body, the unit is able to transmit the series of pulses in a silent way and at any moment to the user's body.

The terms at "which time" as referred herein means any period of time (an interval or a specific time), in particular appropriate for the administration of a medicine. For example, this could be at 8:00 AM, at 2:00 PM, at 8:00 PM and at 0:00 AM, or even every hour, every two hours, twice a day, a night, or the like.

The term "pulses" as mentioned herein comprises several different stimuli such as electric pulses, vibrations, temperature changes, every stimuli implying senses of the human or mammalian being, in a continuous, interrupted or periodic manner, preferably in an interrupted or periodic manner and most preferably in a periodic manner.

Such an electric communication unit is further completely independent of a base unit after being (pre-)programmed. In fact, a user has just to enter the appointments or the administration time via the emitting base unit which will transmit a signal to a receiver-antenna of the electric communication unit. Said receiver-antenna is connected to the pulse generator comprising a processing unit with a memory. The memory is provided to store the second signal, containing information/data indicative at which time the first signal (activation signal) should be generated. Since the data is stored in the memory of the processing unit, the processing unit will generate an activation signal (which is the said first signal) when required, without requiring to be within the transmission range of the base unit. The first signal (activation signal) can be generated at the same time as the second signal (information/data signal) when required or at a later moment when required. In other words, the communication unit operates independently from the distance between the base unit and the receiver. Once programmed and initially activated, the electric communication unit functions autonomously.

It should be appreciated by those skilled in the art that the second signal and the activation (first) signal may be the same or different signals. In GB 2 386 207, these two signals are in fact a single signal. According to the invention, these signals could be different, but are not necessarily different. The activation signal (first signal) results from the second signal emitted by the base unit, which has been processed by the processing unit and stored in the memory to be sent in an appropriate time during the day or the night to the body contacts.

Moreover, it is not necessarily the patient who wears the electric communication unit. In the case of a medication for children, it can be advantageous that the unit is applied on the skin of parents to be certain that the medication is correctly administered to the children and, for example, during night, it is more suitable that parents wake-up upon reception by body contacts of the series of pulses rather than children.

In a particular embodiment, the pulse generator comprises a voltage source for generating said series of pulses. The series of pulses having preferably a voltage range from 20 Vdc to 150 Vdc, more preferably from 50 Vdc to 100 Vdc and most preferably around 75 Vdc.

This can be advantageous to have a series of pulses which are noticeable for the person but not for the surrounding person to allow discretion.

In a particularly advantageous embodiment, the pulse generator comprises a current source for generating said series of pulses.

The presence of a current source allows the delivery of a constant intensity which is very benefic. Indeed, the skin of each person is different and while some people will sense the series of pulses, other will be very sensitive to the pulses or even will not sense the pulses. Moreover the voltage is the result of the product of the value of the resistance and of the value of the intensity of the current. By imposing a constant voltage to the skin, if the resistance of the skin changes for a reason or another, the intensity of the current could be greater or smaller that the one which is intended to apply. Therefore, it is advantageous to provide a constant intensity of current to the skin, which will be comprised between the hereafter mentioned values.

Preferably, the series of pulses has an intensity range from 1 mAdc to 150 mAdc, more preferably from 10 mAdc to 50 mAdc and most preferably around 30 mAdc.

The ranges are advantageous for allowing discretion while being acceptable and noticeable for the person wearing the unit.

Preferably, the pulse generator comprises a current limiter.

The presence of the current limiter improves security by avoiding a too high intensity to be applied onto the skin.

The device according to the invention allows discretion, indeed only the user perceives the activity. No other person will notice the alert signal (series of pulses). Moreover, this feature allows the unit to be particularly safe.

Furthermore, the pulses have a width comprised between 1 μs and 10 ms, preferably between 10 μs and 1 ms, and most preferably around 30 μs and wherein the period between pulses ranges from 1 μs to 10 s, preferably from 100 μs to 100 ms, and most preferably around 1 ms.

By this way, the generated impulses are enough effective to be noticed by awakened and if needed by sleeping people.

Advantageously, said series of pulses further comprises a plurality of bursts, each burst comprising a set of pulses, said bursts being separated form each other by a period of time without pulses. This allows to spread the output electric current, for example, in order to gently awake sleeping people or to not surprise working people, etc.

Preferably the patch comprises an adhesive layer such as Macfilm F 2023 commercially available from MACTAC®, or the like. By the use of such an adhesive layer, the patch is hypoallergenic and resistant to soapy water, alcohol, to some hydrocarbons, etc. In a variant embodiment of the invention, the electric communication unit further comprises an area being a membrane on which a drug is adsorbed, said electric communication unit being further provided to be used as a transdermal patch.

It can be advantageous to combine the benefit of a transdermal patch with the electric communication unit. In this embodiment, the electric communication unit is for example provided to alert the patient that the patch has to be replaced.

In a very particular advantageous embodiment, the electric communication unit further comprises biosensors or nanochips provided to measure biological, chemical and/or physical data and to transmit said data to the memory.

For example, there exist some sensors being able to quantify the protein or glucose content by their electrochemical properties. Therefore, in the case of a diabetic patient, the electric communication unit shall be able to remind the patient that he or she has to make his or her insuline injection and the unit can also confirm that the normal glucose level is now well achieved as a result of a well done and effective injection.

The biosensors or nanochips, for example working on the conductivity of several biological substances can detect several biological, chemical and/or physical parameters such as the protein level, the enzyme level, the dissolved oxygen, the arterial pressure, and the like. All the existing biosensors or nanochips can be used in the present invention. The biosensors or the nanochips or even biometric captors are provided to send a third signal containing a value of a biological, a chemical or a physical parameter to the processing unit. The processed third signal being provided to be stored in the memory and to be extracted, for example by the doctor or by the patient. In an alternative embodiment, the processed third signal stored in the memory is transmitted to a comparator for being compared to a normal stored value of this biological, chemical or physical parameter and when both values are similar or the value of the third signal (parameter signal) is within a range of acceptable values from said normal value, the comparator will transmit a confirmation signal meaning that the normal value was reached to the processing unit. The processing unit will send a further activation signal to the pulse generator which will generate a confirmation series of pulses being identical or different from said series of pulses to inform the patient that the normal value is reached.

In still a variant embodiment, the processed third signal stored in the memory is transmitted to a comparator for being compared to a normal stored value of this biological, chemical or physical parameter and when both values are different or outside the range of acceptable values from said normal value, the comparator will transmit an alarm signal meaning that an abnormal value was reached to the processing unit. The processing unit will send an activation signal to the pulse generator which will generate an alarm series of pulses being identical or different from said series of pulses to inform the patient that an abnormal value for the biological, chemical or physical value is reached.

Preferably, the electric communication unit according to the invention also comprises recording means provided to store and to transmit to the memory a confirmation data.

It can be advantageous that the recording means are able to store and to transmit to the memory a confirmation data for example concerning the number of times that the pulses have been transmitted, the time at which the series of pulses have effectively been generated and if the series of pulses has effectively been transmitted to the skin.

This can find an application for insurance companies which can require to have a confirmation that the patient has effectively taken his or her medicine at a predetermined interval of time, for example when refunding of costs subjected to conditions.

Moreover, the unit according to the invention can also find an application for nurses wearing the electric communication unit for reminding them to administer the medicine to a patient. Therefore, the risk that a nurse will forget the administration is decreased.

Moreover, the invention relates to an electric communication system comprising said electric communication unit and a base unit, wherein the electric communication unit comprises a receiver or a receiver-antenna and wherein said base unit is a wireless transmitter to transmit said second signal to the receiver or to the receiver-antenna of said electric communication unit without opening a unit packaging enclosing said electric communication unit.

This covers different advantages of the invention. First, in the case of an individual packaging provided for the patch, which patch was programmed in a wireless manner through the packaging, the user is ensured that the patch is a new one and the hygienic conditions are respected. Moreover, this packaging protects the patch from sun, moisture, etc. which can damage the adhesive layer or the like. Secondly, in some cases, the medicine packaging may contain one or more electric communication units according to the invention. The wireless programming allows the pharmacist to program the unit without opening the medicine packaging.

In an advantageous embodiment the wireless communicated information between base unit and electric communication unit can be encrypted to improve the security and confidentiality of the user.

Furthermore, when several patches are provided into a medicine therapy, they should advantageously contain an identifier allowing each patch for being differently programmed by suitable means. For example, the therapy may comprise the administration of a tablet twice a day during the first week, once a day during the second week, etc. By using patches with identifiers, this allows the pharmacist to program respectively the first and the second patch according to the instructions of the doctor.

The points in time of activation (i.e; the time at which the first signal (activation signal) should be generated) or the frequency have to be easy programmable. Several means can be used to program the unit according to the invention. This could be done during manufacturing by hard coding the content of the memory, or “on site” at user location or also for example, by the pharmacist when selling some medicine. By hard coding during manufacture, the power source of the unit according to the invention is advantageously not used during this step. The wireless transmitter can be an RF transmitter, an inductive transmitter, a capacitive transmitter, an infrared transmitter, an acoustic transmitter or the like, comprising means allowing to program while avoiding the opening, for example, of the medicine or of the patch packaging. The most preferred transmitter is an inductive RF transmitter since it does not use the power source of the communication unit when storing the data into the memory. Preferably, the patch and the patch packaging are provided with predefined dimensions to be added to plenty of existing medicament packaging. Of course, patches included into the medicine packaging can also be pre-programmed during manufacturing (hard coded).

Furthermore, the invention relates also to the use of the electric communication system according to the invention in a medicine therapy to remember the timely administration of a medicine.

The use in a medicine therapy as referred herein comprises either the use in which the patch is used to remind the patient to take his or her medicine, the use in which the patient wears a separate transdermal patch and in which the patch reminds the patient that his or her transdermal patch should be changed or replaced or another use in which time could be an important factor. Moreover, the adhesive layer of the patch according to the invention may comprise various active agents usually used in a conventional transdermal patch therapy. This means that in common patches, the active agent is combined, possibly by using a membrane layer, with the adhesive layer to penetrate to the skin of a person. The patch according to the invention can be manufactured in such a manner that the adhesive layer of the patch also comprises the active agent. By this way, the electric communication unit (the patch) will remind the patient to remove or to replace his or her patch. Moreover, as mentioned before, the electric communication unit in the shape of a patch can be used by parents or nurses to ensure that children or patient actually take their medicine on time.

In a variant, the electric communication unit can be used as a wake-up device. This allows to wake-up only one person when several persons are sleeping in the same room and to preserve the sleeping time of the others. Further, the unit can also be used, for example, to educate a dog for learning it to wake-up and go out when required during the night or at any other period of the day, or to any other end in which reminding of time is essential or required.

In addition, the cost of the patch can be low in comparison with the cost of the medicine.

In a variant embodiment, the electric communication unit or the electric communication system can be used in a LAN (local area network) or a BAN (body area network). For example, in an hospital, the doctor can determine the administration of medicine for several patients and attribute a different series of pulses to each patient. Then, the nurse has just to program the patches by means of a base unit. As a result, each patient will receive his or her corresponding series of pulses.

Moreover, in an alternative embodiment, the invention provides a central electric communication unit, for example provided to be used by a nurse, and a series of secondary electric communication units, for example provided to be worn by patients. The nurse, as mentioned before, will receive a particular series of pulses corresponding to a particular patient, and the patient wears the aforementioned electric communication unit with biosensors or nanochips. The biosensors or nanochips will emit the third signal (parameter signal) containing a value of a biological, a chemical or a physical parameter to the processing unit which will emit them to a central base unit comprised in the LAN or in the BAN. Therefore, it can be possible to verify the reliability of the nurse or the compliance of the patient. This verification can be useful in some cases of medical error or other where it should be required to prove administration of a medicine.

Therefore, the electric communication unit or the electric communication system can be used as a medical control and follow-up device or as a confirmation device. Other embodiments of the electric communication unit or system according to the invention are mentioned in the annexed claims.

Other characteristics and advantages of the invention will appear more clearly in the light of the following description of particular non-limiting embodiments of the invention, while referring to the figures.

BRIEF DESCRIPTION OF THE DRAWINGS

FIG. 10 is a graphic illustrating a possible memory allocation.

Figure 1:
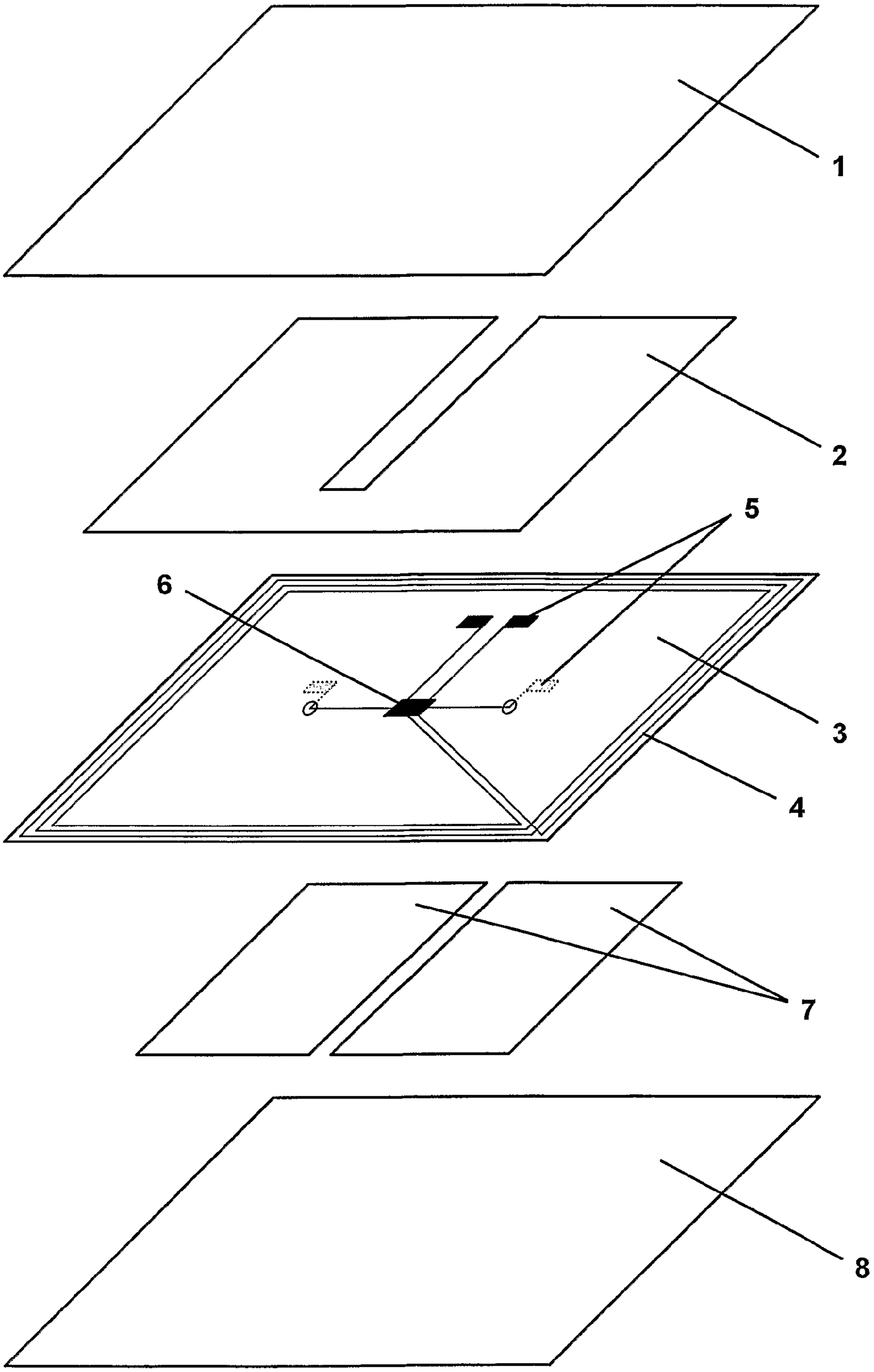
FIG. 1 is an exploded view of the device according to the invention.

In the drawings, a same reference sign has been allotted to a same or analogous element of the electric communication unit or system according to the invention.

DETAILED DESCRIPTION OF THE INVENTION

The invention concerns a patch, in particular a thin (self)-adhesive patch which is stick to the user's skin. The patch generates at pre-programmed or free programmable moments pulses. These pulses are felt by the human skin and remind the user to undertake a certain action, for example administrating a medicine.

Figure 2:
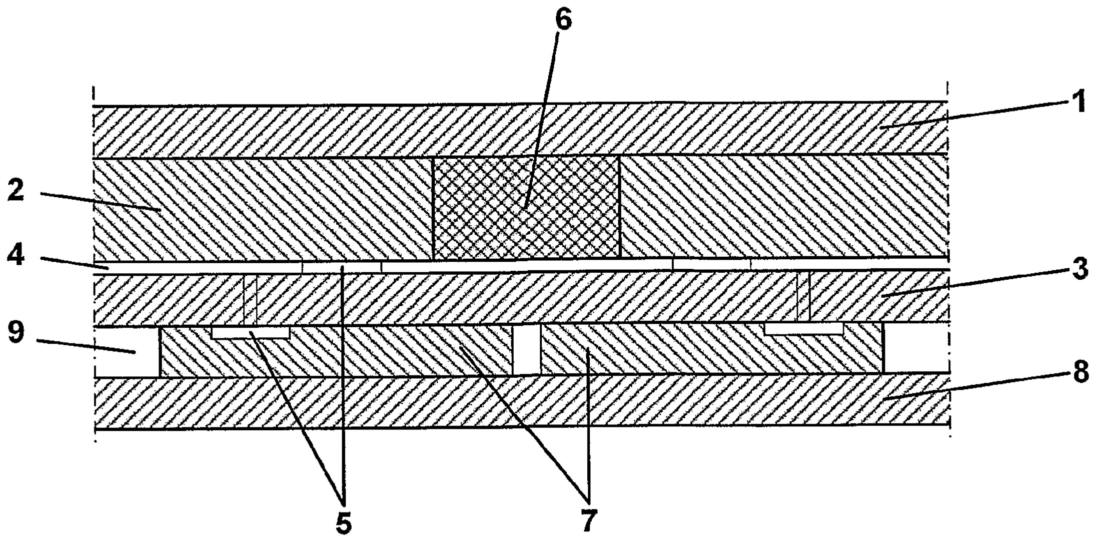
FIG. 2 is a transversal section of the device according to the invention.

FIG. 1 and FIG. 2 show the components of the patch.

The support element 3 consists of a thin flexible synthetic material and is used as a printed circuit board (PCB). The design of this PCB integrates a receiver-antenna 4, the contact elements 5 for generating contacts between the power supply 2 and the body contacts 7. The electric components/ASIC (Application Specific Integrated Circuit) 6 are positioned on the support element 3 and connected with the power supply 2, the receiver-antenna 4 and the body contacts 7. The electric components/ASIC is forming the pulse generator 6. The cover I consists of a thin flexible synthetic material and is used to protect all fragile electronic components against external influences. An adhesive 9 is added on the bottom side of the support element 3. The liner 8 consists of a thin flexible synthetic material and is adhered to the adhesive 9 during the preservation of the patch. The liner 8 is removed just before the moment of application to the user's body. The adhesive 9 keeps the patch adhered to the skin during the time of use.

Figure 3:
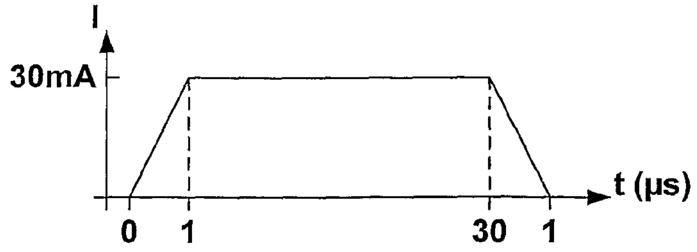
FIG. 3 is a graphic illustrating a preferred pulse shape for the set of pulses.

The pulse generator of the patch generates at well-determined moments a series of electric pulses. Each pulses has preferably a block wave form with the following properties as it can be seen at FIG. 3:

- pulse width: preferably from 1 μs to 10 ms, more preferably from 10 μs to 1 ms, and most preferably about 30 μs.
- period between pulses: from 1 μs to 10 ms, preferably from 100 μs to 100 ms and more preferably about 1 ms.
- intensity of the current: preferably from 1 mAdc to 150 mAdc, more preferably from 10 mAdc to 50 mAdc and most preferably about 30 mAdc.
- in the case of a voltage source, the voltage should be preferably from 20 Vdc to 150 Vdc, more preferably from 50 Vdc to 100 Vdc and most preferably around 75 Vdc.
- raising time: preferably less than 5 μs, more preferably less than 1 μs.
- falling time: preferably less than 5 μs, more preferably less than 1 μs.

Figure 4:
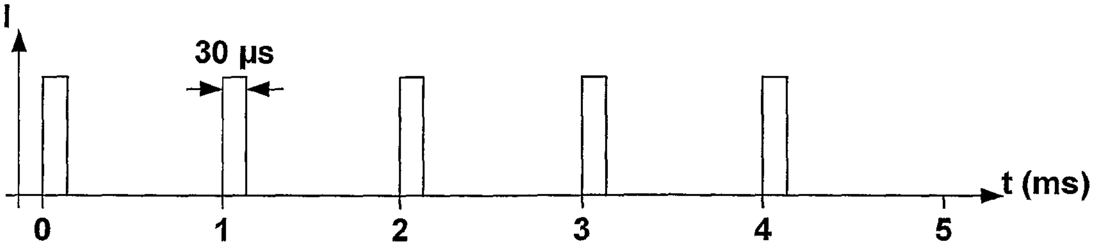
FIG. 4 is a graphic illustrating a possible burst of the set of pulses.

As it can be seen on FIG. 4, a burst comprises a set of pulses. Exemplary values are the following: a burst preferably consists of 500 pulses with a pulse duty-cycle of 30 μs/1 ms. The duration of a burst is generally consequently 500 ms.

Figure 5:
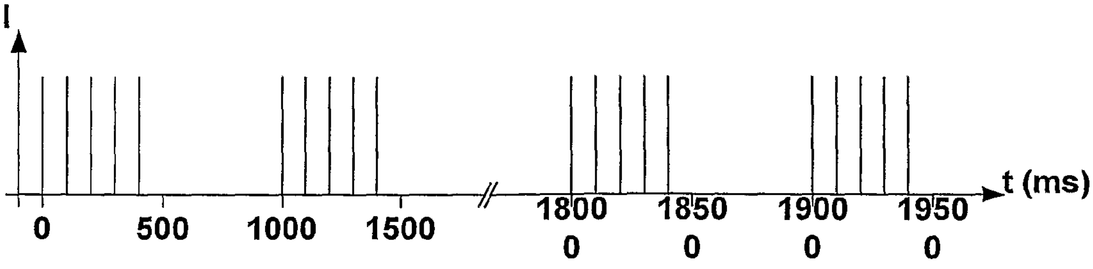
FIG. 5 is a graphic illustrating a possible activation scheme of the series of pulses.

A series of bursts forming said series of pulses is called an activation, such an activation can be seen at FIG. 5. This latter preferably consists of 20 bursts with a duty-cycle of 500 ms/1 s. The duration of an activation is consequently 20 s. Each burst in this case comprises a set of 500 pulses.

The time at which the activation signal should be generated or the interval of times are determined by means of a programming device or a base unit.

Figure 6:
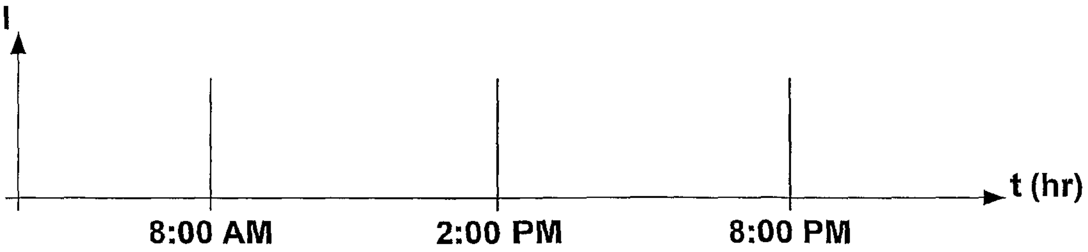
FIG. 6 is a graphic illustrating a possible daily scene.

A possible daily scene is illustrated in FIG. 6. This is an exemplary profile of the series of pulses, but those skilled in the art should understand that it could be different. For example, each burst can be different, each burst can comprise a different number of pulses, each series can be also different, and furthermore, the differences can be used to remember different step of the therapy, for example, 5 times three pulses or 20 short bursts could indicate to take the medicine and 3 times four pulses or 5 long bursts could indicate to remove another patch (a transdermal one) or the patch itself.

In a variant, 20 short bursts can be attributed to a particular patient A, 10 short bursts can be attributed to a particular patient B and 3 long bursts to a third particular patient. Then the electric communication unit worn by a nurse reminds him or her to administer the medicine to the particular patient A, B or C.

The clock's drift is preferably at most 1/10,000 (100 ppm). This means approximately 1 minute per week.

In case the internal clock isn't accurate enough, a measurement of the clock frequency will be necessary after manufacture. With this measured data a value can be put into the memory fixing the counter's end value (for example a clock correction factor) which represents for example a burst frequency of 1 Hz. This action preferably takes place at the patch factory. Executing this action during programming of the activation implies indeed that every programming device has to be equipped with an expensive measurement system for frequency or time.

About 200 activations (8-Bit address-bus) with an accuracy of 10 s must be able to be programmed. This means that a 16-Bit data bus is needed for a weekly schema (2^16=65536).

Alternatively, 128 activations (7-Bit used out of an 8-Bit address-bus) with an accuracy of 1 minute must be able to be programmed. By means of 15-Bits used out of a 6-Bit databus (2^15=32768), the maximum use is 3 weeks.

The programming of the chip uses wireless technology, identical to the system used for programming of an (active) RFID tag. The distance between the base unit and the patch is small. The maximum distance is preferably less than 0.2 m to avoid interference with current applications.

In the case of a central base unit comprising a server, the distance between the programming means and the patch can be longer.

After the unit has been programmed, the receiver or the receiver or receiver-antenna can be temporary detached or deactivated to avoid interference with current or other applications. The duration of the inactivity of the antenna can be stored in the memory during the programming.

The pulse generator may advantageously comprise a receiver integrated therein, but it should be noted that the pulse generator may also be connected to a receiver, external to said pulse generator. The receiver should not specifically be present into the unit once programmed. The receiver could be removed after programming or can be completely independent. If the programming of the unit is hard coded during manufacturing, no receiver is required in the electric communication unit according to the invention.

The energy needed for programming the (EE)PROM is, for example, delivered by the programming device (for example the base unit) by means of inductive coupling. A few examples of existing chips with a similar goal are given at Table 1.

TABLE 1

| | |
|---|---|
| Atmel | T555714-DBW |
| EM Microelectronics | EM4450 |

These chips need to be modified with an external access to the memory. The principle of programming is identical.

Before the chip is operated, only a very small leakage current is permitted to not discharge quickly the power supply. The power supply could be any type of portable power supply, such as battery and the like. This can be a rechargeable or a non rechargeable depending on the duration of the use, the cost of the unit and the dimensions of the unit for a particular application.

Because the input voltage is low (3V) and a relatively high output voltage is needed a voltage converter is used. Some examples of possible existing chips with a similar goal are given on Table 2.

TABLE 2

| Producer | Product type |
|---|---|
| Micrel | MIC4826 |
| Supertex | HV826X or HV850 |
| Panasonic | MIP804 |
| NPC | SM8142BD |
| Sipex | SP4403 |
| Toko | TK65915M |
| Zywyn | ZSP4403UEB |

To reduce the dimensions of the electric circuitry it is recommended to use an ASIC.

Figure 7:
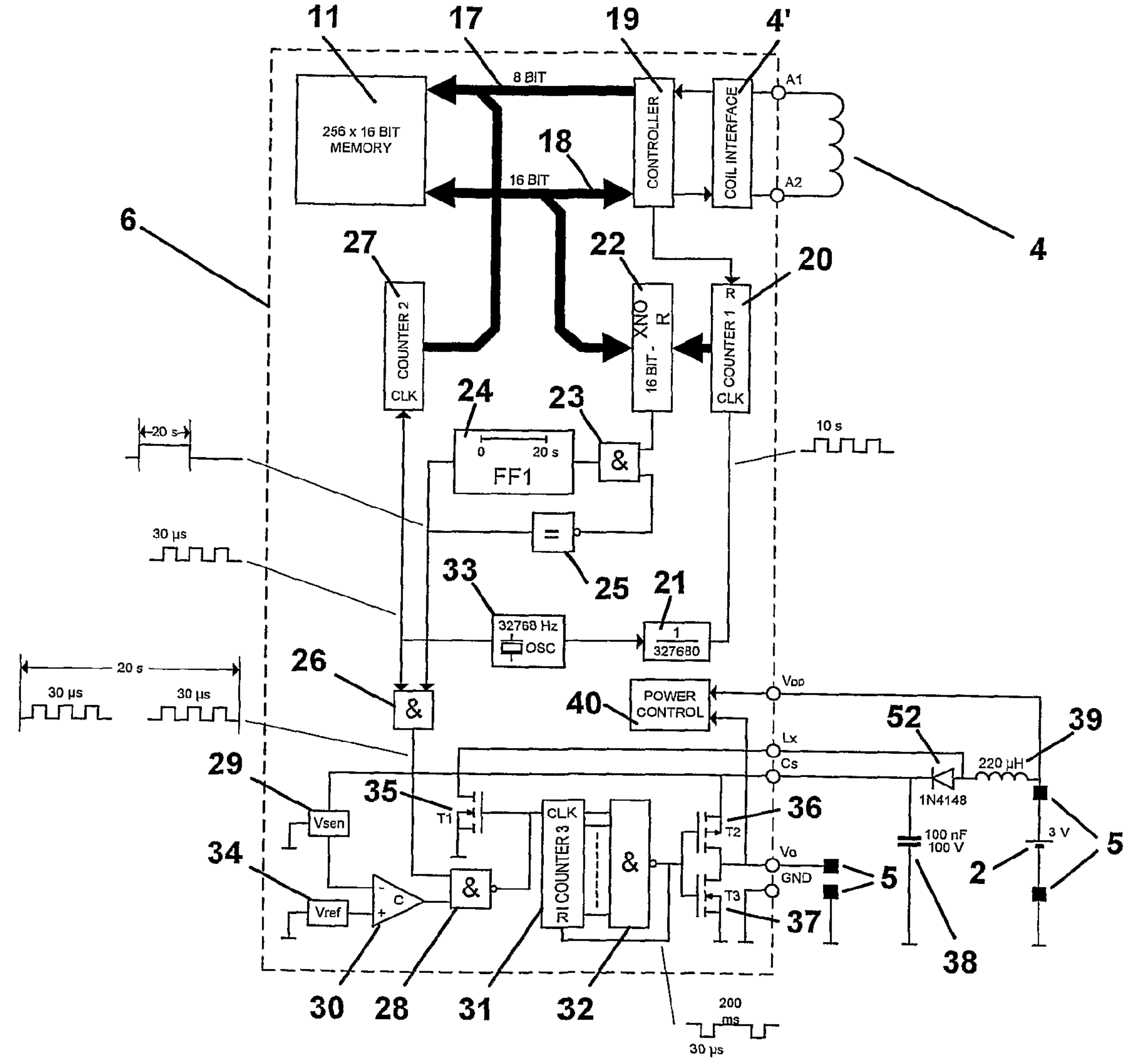
FIG. 7 is a schematic view of a first possible concept of the electric circuitry.

A first possible concept is shown in FIG. 7.

The first possible concept is a generation of high voltage by use of induction. Hereto a set of discrete components (coil, diode and capacity) are needed. As already mentioned, the electric components/ASIC are forming the pulse generator 6. The electric components/ASIC (Application Specific Integrated Circuit) 6 are connected with the power supply 2, the receiver-antenna 4 and the contacts 5. The contacts 5 are provided to be connected to the body contacts 7 and the power supply being a battery 2.

The pulse generator 6 comprises a memory 11, which is connected to a first end of an 8-Bit address-bus 17 and to a first end of a 16-Bit data bus 18. A second end of the 8-Bit address-bus 17 and of the 16-Bit data bus 18 are connected to a controller 19. The controller is connected to a coil interface being a receiver 4', connected to an antenna 4.

The controller 19 is connected to a reset input of a first clock counter 20. A clock input of the first counter 20 is connected via a divider 21 to the clock 33 itself. An output of the first clock counter 20 is connected to a first input of a comparator 22. A second input of the comparator 22 is also connected to the 16-Bit data bus 18. An output of the comparator 22 is connected to a first input of an AND-gate 23. An output of the AND-gate 23 is connected to a flip-flop FF1 24. An output of the FF1 24 is connected to an input of the inverter 25, the output of the inverter 25 is connected to a second input of the AND-gate 23. The output of the FF1 24 is also connected to a first input of a second AND-gate 26.

The 8-Bit data bus 17 is connected to a second clock counter 27 which clock input is connected directly to the clock 33.

A second input of the AND-gate 26 is also directly connected to the clock 33. An output of the AND-gate 26 is connected to a first input of a NAND-gate 28. A voltage reference Vref 34 is connected to a positive input of a comparator "C" 30. A negative input of the comparator "C" 30 is connected with the voltage conditioner Vsen 29. The output of the comparator "C" 30 is connected to a second input of the NAND-gate 28. An output of the NAND-gate 28 is connected to a clock input of a third clock counter 31 and to a gate of a switching transistor T1 35. An output of the third clock counter 31 is connected to inputs of a second NAND-gate 32. An output of the NAND-gate 32 is fed back to a reset input of the third clock counter 31 and is also connected to gates of two switching transistor elements T2 36 and T3 37.

The power supply 2 is connected to a power control 40. An input of the power control 40 is connected to an output voltage.

The power supply is also a voltage source for a voltage booster formed by a coil 39, a diode 52, the switching transistor T1 35 and a capacity 38.

In the first phase the memory 11 of the ASIC (Application Specific Integrated Circuit) is programmed. In here the points in time of activation are recorded. The used technology is identical to that for programming of RFID tags (Radio Frequency Identification tags). The energy needed for programming the communication unit according to the invention is delivered by a programming device (base unit) by means of inductive coupling. The memory 11 can be (pre)programmed during in particular the production process of the ASIC or in a later phase during delivery by means of a programming device. The hardware of this programming device is similar to that of an RFID-programmer. The software, offering a user-friendly way of programming, calculates the data to be stored in a memory 11 using the given points in time.

The ASIC is only put in operation at the moment of first use of the patch. This is done to keep the power consumption minimal when not in use. Starting the ASIC is managed by the block "power control" 40 of the ASIC. The start of the ASIC is based on the principle that, at the moment of first application on the skin, a small leakage current is caused which triggers the ASIC in operation.

Once the ASIC has started, both first clock counter 20 and second clock counter 27 begin to count. The first clock counter 20 is a binary 8-bit counter and counts with a frequency of 32768 Hz. The second clock counter 27 ensures that all memory locations (256) are read out in a sequential way. The flip-flop FF1 24 is set when one of the 256 values is equal to the value of the first clock counter 20. After 20 seconds, FF1 24 is reset.

If the flip-flop FF1 24 is set and the comparator "C" 30 is high the clock-pulses are transported to the first switching transistor T1 35. The first switching transistor T1 35 is now switching during 20 seconds with a frequency of 32768 Hz. The result is the generation of a high voltage by self-induction of the coil 39. The capacity 38 is charged up to a voltage of about 75V.

Figure 8:
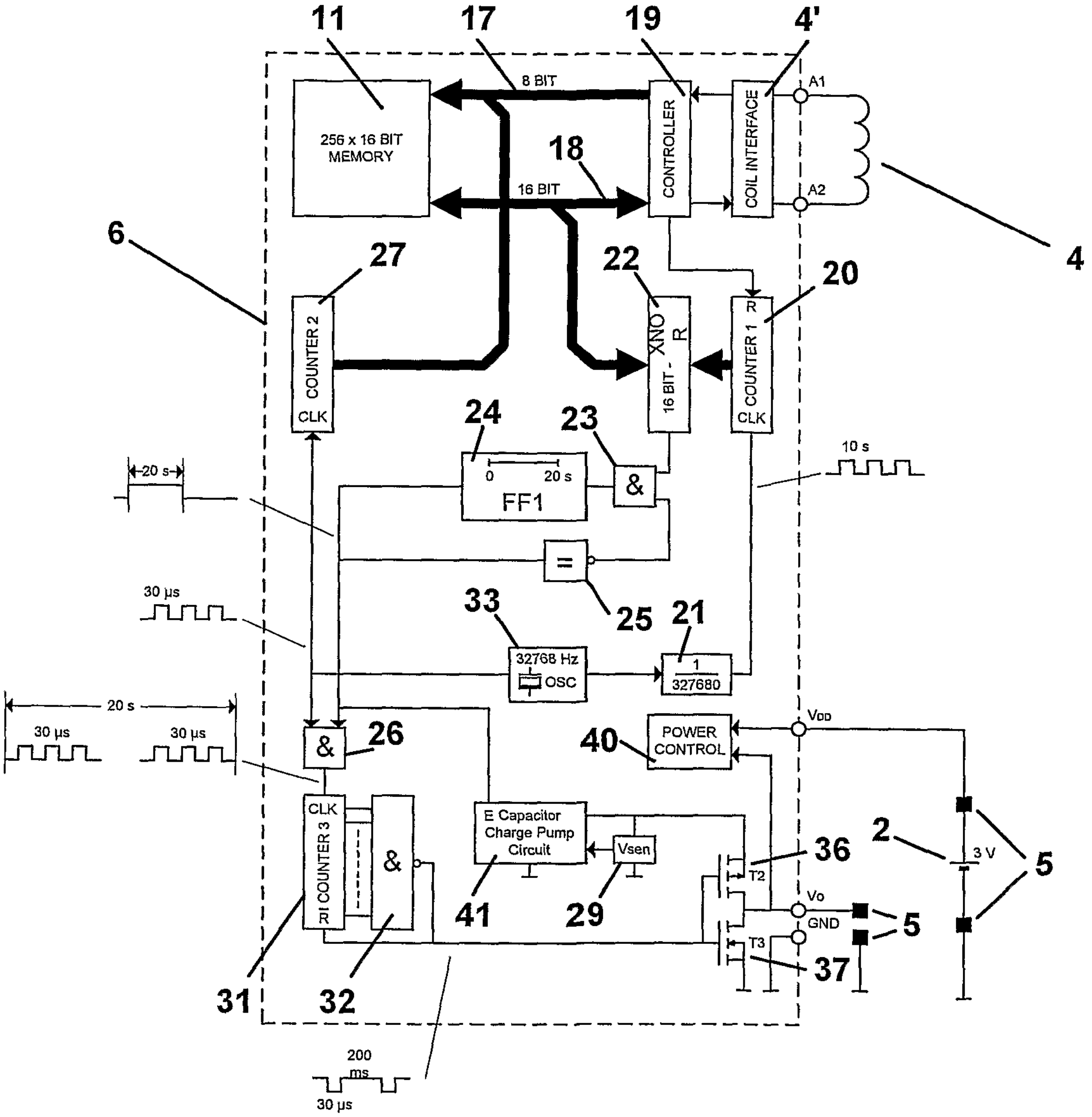
FIG. 8 is a schematic view of a second possible concept of the electric circuitry.

FIG. 8 illustrates a second possible concept using a capacity charge pump which can be incorporated in the ASIC itself (for example, HV 850 available from Supertex).

The pulse generator 6 comprises the memory 11, which is connected to the first end of 8-Bit address-bus 17 and to the first end of a 16-Bit data bus 18. The second end of the 8-Bit address-bus 17 and of the 16-Bit data bus 18 are connected to the controller 19. The controller is connected to the coil interface being the receiver 4', connected to the antenna 4.

The controller 19 is connected to the reset input of the first clock counter 20. The clock input of the first counter 20 is connected via the divider 21 to the clock 33 itself. The output of the first clock counter 20 is connected to the first input of the comparator 22. The second input of the comparator 22 is also connected to the 16-Bit data bus 18. The output of the comparator 22 is connected to the first input of an AND-gate 23. The output of the AND-gate 23 is connected to the flip-flop FF1 24 . The output of the FF1 24 is connected to the input of the inverter 25, the output of the inverter 25 is connected to the second input of the AND-gate 23. The output of the FF1 24 is also connected to the first input of a second AND-gate 26.

The 8-Bit data bus 17 is connected to the second clock counter 27 which clock input is connected directly to the clock 33.

The second input of the AND-gate 26 is also directly connected to the clock 33.

The output of the AND-gate 26 is connected the third clock counter 31 which is connected to the NAND-gate 32. The output of NAND-gate 32 is in contact with the gates of two switching transistor elements T2 36 and T3 37.

The output of the FF1 24 is also connected to an enable input of a Capacity Charge Pump 41. An output of the Capacity Charge Pump 41 is connected to the source of T2 36.

The power supply 2 is connected to the power control 40. The input of the power control 40 is connected to the output voltage.

Vsen 29 is a voltage conditioner to regulate the output voltage of the Capacity Charge Pump 41 and is connected to the Capacity Charge Pump 41.

If the flip-flop FF1 24 is set, then the Capacity Charge Pump 41 is enabled and will generate the desired output voltage which is lead to the switching output-stage T2 36 and T3 37.

In both cases (FIG. 7 and FIG. 8), the third clock counter 31 and the NAND-port 32 manage the desired duty-cycle of the output voltage. The transistors T2 36 and T3 37 are used as output-stage.

Figure 9:
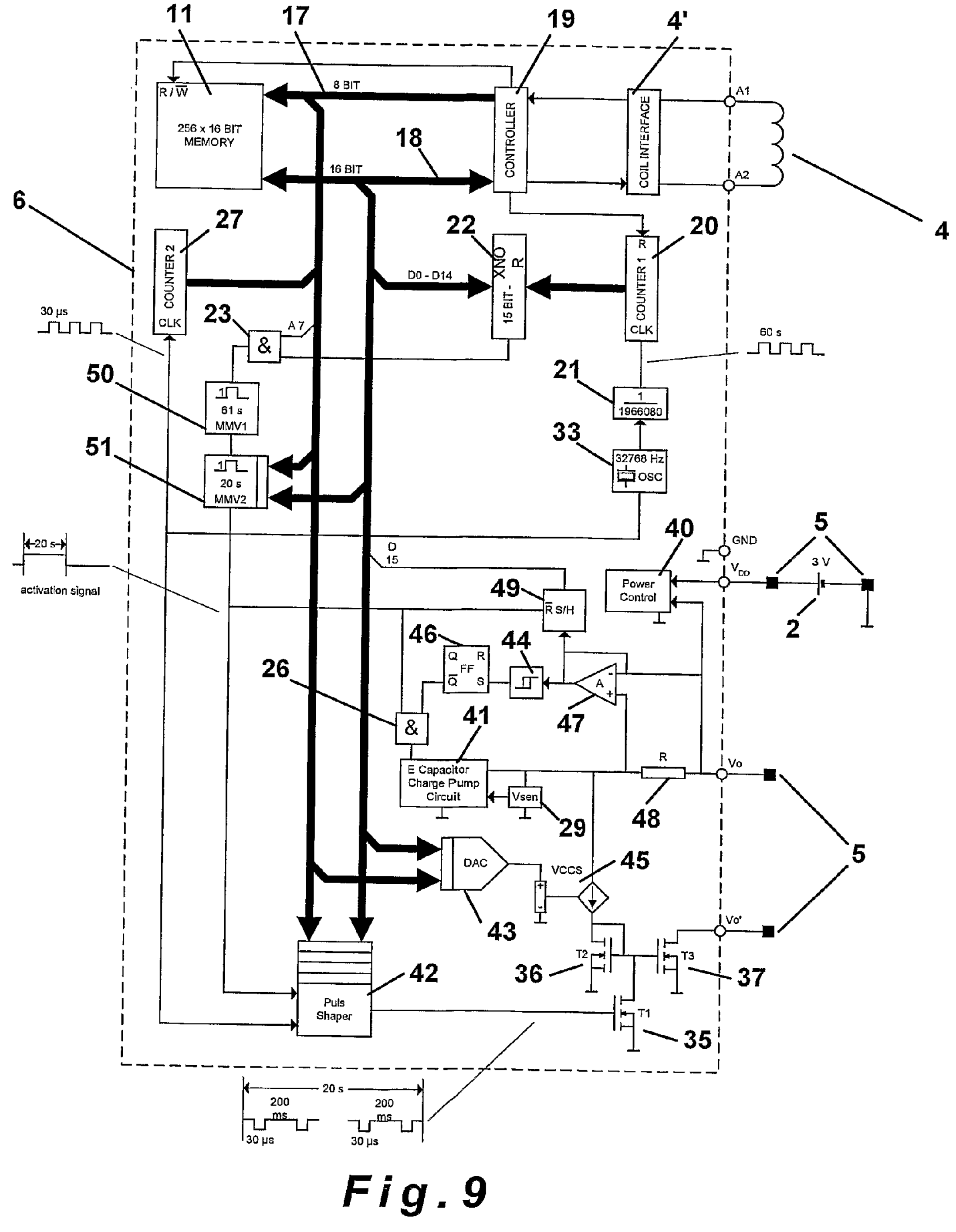
FIG. 9 is a schematic view of a third possible concept of the electric circuitry.

As it can be seen in FIG. 9, the third possible concept uses a number of improved features. These extra functionalities are:

1) a current source instead of a voltage source.

2) a current detector to be used in:

a control mechanism to check whether or not the electric communication unit has worked correctly.

a safety mechanism to avoid undesirable high electro shocks.

3) programmable pulse pattern.

4) programmable strength of current.

As it can be seen at FIG. 9, which figure should be encompassed with FIG. 10 describing the different parts of the memory, the pulse generator 6 comprises the memory 11, which is connected to the first end of 8-Bit address-bus 17 and to the first end of a 16-Bit data bus 18. The second end of the 8-Bit address-bus 17 and of the 16-Bit data bus 18 are connected to the controller 19. The controller is connected to the coil interface being a receiver 4', connected to an antenna 4.

The controller 19 is connected to the reset input of the first clock counter 20. The clock input of the first counter 20 is connected via the divider 21 to the clock 33 itself. The output of the first clock counter 20 is connected to the first input of the comparator 22. The second input of the comparator 22 is also connected to the 16-Bit data bus 18. The output of the comparator 22 is connected to the first input of an AND-gate 23. The other input of the AND-gate 23 is connected to A7 of the address-bus. The output of the AND-gate 23 which on its turn is connected to a first monostable multivibrator 50 and to a second monostable multivibrator 51 placed in series. The output of the second monostable multivibrator 51 is connected to a first input of a pulse shaper 42 and to the AND-gate 26.

The 8-Bit data bus 17 is connected to the second clock counter 27 which clock input is connected directly to the clock 33.

The second input of the pulse shaper 42 is also directly connected to the clock.

The monostable multivibrator 51, the pulse shaper 42 as well as a digital-analog converter “DAC” 43 are connected to the 8-Bit data bus 17 and the 16-Bit data bus 18.

The digital-analog convertor “DAC” 43 is connected to a voltage controlled current source (VCCS) 45 that is connected to a resistor 48 and to an output of the capacitor charge pump circuit 41.

Two inputs of an operational amplifier 47 are connected with two sides of the resistor 48. An output of the operational amplifier 47 is connected via a Schmitt-trigger 44 to a set input of an RS flip-flop 46 and to an input of a sample and hold function “S/H” 49. A negated output of the RS flip-flop 46 is connected to the second input of the AND-gate 26. The output of the AND-gate 26 is connected to the enable input of the capacitor charge pump circuit 41.

The power supply 2 is connected to the power control 40. The input of the power control 40 is connected to the output voltage.

Vsen 29 is the voltage conditioner to regulate the output voltage of the Capacity Charge Pump 41 and is connected to the Capacity Charge Pump 41.

The output of the sample and hold function “S/H” 49 is in communication at data line D15 with the memory. The reset input is connected with an output of the second monostable multivibrator 51.

The current of the voltage controlled current source VCCS 45 flows through the transistor T2 36. Transistor T3 37 forms a current mirror with transistor T2 36. As a result the same intensity of current flows through transistor T2 36 as through transistor T3 37 and via the body contacts 7 through the skin.

An output of the pulse shaper is connected to the gate of transistor T1 35. This transistor T1 35 switches the output current on and off in a way determined by the pulse shaper. For this, the source of T1 35 is connected to the gates of the transistors T2 36 and T3 37.

In the first phase the memory 11 of the ASIC (Application Specific Integrated Circuit) is programmed. The points in time of activation are recorded herein. The used technology is identical to that for programming of RFID tags (Radio Frequency Identification tags). The energy needed for programming the communication unit according to the invention is delivered by a programming device (base unit) by means of inductive coupling. The memory 11 can be (pre)-programmed during in particular the production process of the ASIC or in a later phase during delivery by means of a programming device (base unit). The hardware of this programming device (base unit) is similar to that of an RFID-programmer. The software, offering a user-friendly way of programming, calculates the data to be stored in a memory 11 using the given points in time.

The ASIC is only put in operation at the moment of first use of the patch. This is done to keep the power consumption minimal when not in use. Starting the ASIC is managed by the block “power control” 40 of the ASIC. The start of the ASIC is based on the principle that, at the moment of first application on the skin, a small leakage current is caused which triggers the ASIC in operation.

Once the ASIC has started, both first clock counter 20 and second clock counter 27 begin to count. The first clock counter 20 is a binary 8-bit counter and counts with a frequency of 32768 Hz. The second clock counter 27 ensures that all memory locations (256) are read out in a sequential way.

The MMV1 (one shot monostable multivibrator) 50 is set when one of the 256 values is equal to the value of the first clock counter 20 and A7 is high. Only D0 to D14 of the data-bus 17 are taken into account because D15 is used to store a verification-bit which indicates whether or not the electric communication unit has worked correctly. Said monostable multivibrator 50 prevents that the output is set multiple times during an exact match between the value of the first clock counter 20 and the content of one of de 256 memory locations (D0 to D14 & A7). Therefore, the duration that monostable multivibrator 50 MMV1 is set must be slightly longer than the clock period of the first clock counter 20. A7 inhibits half of the memory locations which are reserved for additional data such as but not limited to: identifier, strength of current, pulse length, pulse duty cycle, burst length, burst duty cycle, activation length, time of antenna inactivity, clock correction factor, etc. (see FIG. 10).

The set-time of monostable multivibrator 51 MMV2 (one shot monostable multivibrator) can be programmed easily because said monostable multivibrator MMV2 51 is connected to the address-bus 18 and data-bus 17. At a particular address the internal register of said monostable multivibrator MMV2 51 is loaded with the data which corresponds with the content of the memory location at that particular address. In this example the time is set to 20 seconds. This means that said monostable multivibrator MMV2 51 is reset 20 seconds after it was initially set.

The output of said monostable multivibrator MMV2 51 is the activation signal and is connected to the Pulse Shaper 42.

Said Pulse Shaper 42 can be programmed in an identical way as used for said monostable multivibrator MMV2 51.

Said Pulse Shaper 42 produces a pattern of pulses and is connected to the gate of the first transistor T1 35.

The VCCS 45 (voltage controlled current source), DAC (digital-analog converter) 43, the second transistor T2 36 and the third transistor T3 37 form a programmable current source. Said second transistor 36 and third transistor 37 is a current minor. The current strength is set by said VCCS. Said VCCS is set by said DAC 43. Said DAC 43 can be programmed in an identical way as used for said monostable multivibrator MMV2 51 and said Pulse Shaper 42.

When the Capacitor Charge Pump Circuit 41 is enabled by the activation signal and the RS flip-flop "FF" 46 is not set, said Capacitor Charge Pump Circuit 41 provides a compliance voltage for said VCCS 45.

In case an activation signal is present the Pulse Shaper 42 switches the first transistor 35 on and off in a way determined by the programmed pulse pattern.

The output current flows through the resistor "R" 48 and via the body contacts through the skin.

The voltage across said resistor 48 is fed at the differential input of the operational amplifier "A" 47.

The output voltage of said operational amplifier 47 is lead to and conditioned by the sample and hold function "S/H" 49. Said sample and hold function 49 stores the information whether or not the electric communication unit has worked correctly (an electric current has flowed during activation). Said sample and hold function 49 keeps the information as long as the activation signal is present. During this time of activation the value of said sample and hold function 49 is transferred and stored at D15 of the memory location pointed at that moment by the first clock counter 20. As a result, one can verify at a later stage whether or not the electric communication unit has worked correctly for specific points in time of activation.

The output voltage of said operational amplifier 47 is also lead to a Schmitt trigger. Said Schmiff trigger 44 acts together with the RS flip-flop 46 as an electronic fuse and thus as a current limiter to avoid an undesirable high current output. The negated output of said RS flip-flop 46 is low when said RS flip-flop 46 is set. This inhibits the enabling of said Capacitor Charge Pump Circuit 41. It is obvious that said RS flip-flop 46 is not set when the ASIC starts.

Figure 11:
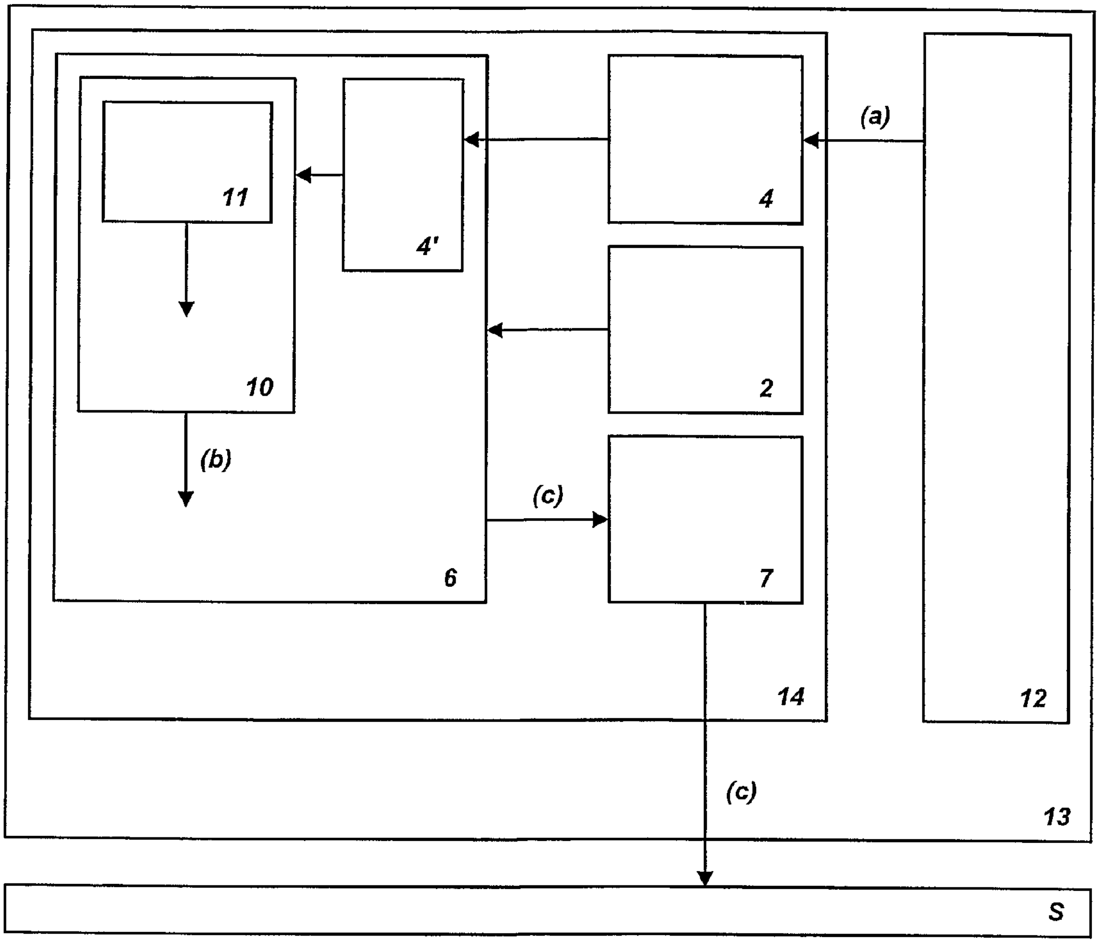
FIG. 11 is a schematic illustration of the electric communication system according to the invention.

As it can be seen in FIG. 11, the electric communication system 13 according to the invention comprises a base unit 12 and at least an electric communication unit 14. The electric communication unit 14, in the form of a PCB unit, comprises a support element comprising the pulse generator 6, the pulse generator 6 comprises a receiver 4' and a processing unit 10. The processing unit 10 comprises a memory 11. The pulse generator 6 is connected to the power supply 2 and to the body contacts 7. Moreover, an antenna 4 is integrated in the electric communication unit 14 and the antenna 4 is directly connected to the receiver 4'. As mentioned before, the electric communication unit can be programmed by the doctor, by the pharmacist, by the patient, by a nurse, or it can be (pre)-programmed by hard coding during manufacturing, for example, when sold with a medication that requires to be administered at predetermined times or time intervals. Therefore, the base unit transmits a data signal (a) (second signal) to the electric communication unit 14. The signal (a) comprises, among other information, data concerning at which points in time the series of pulses have to be generated. The second signal (a) is received by the antenna 4 and transmitted to the receiver 4'. The receiver on its turn transmits the signal to the processing unit 10 to store it in the memory 11. When required, the activation signal, also called herein the first signal (b) is sent to the pulse generator 6. When the pulse generator 6 receives the activation signal (b), current was taken from the power source 2 and a series of pulses (c) (which can also be called alert signal) is generated by the pulse generator 6. The series of pulses is transmitted to the body contacts 7 to transmit said series of pulses to the skin (S) of a wearer of the electric communication unit (the patch) 14 according to the invention.

Therefore, the patient, the children, the elder, the dog, the man, and the like will sense the series of pulses (c) on his/her skin (S), and will become aware that he/she has something to do, to take, etc.

Figure 12:
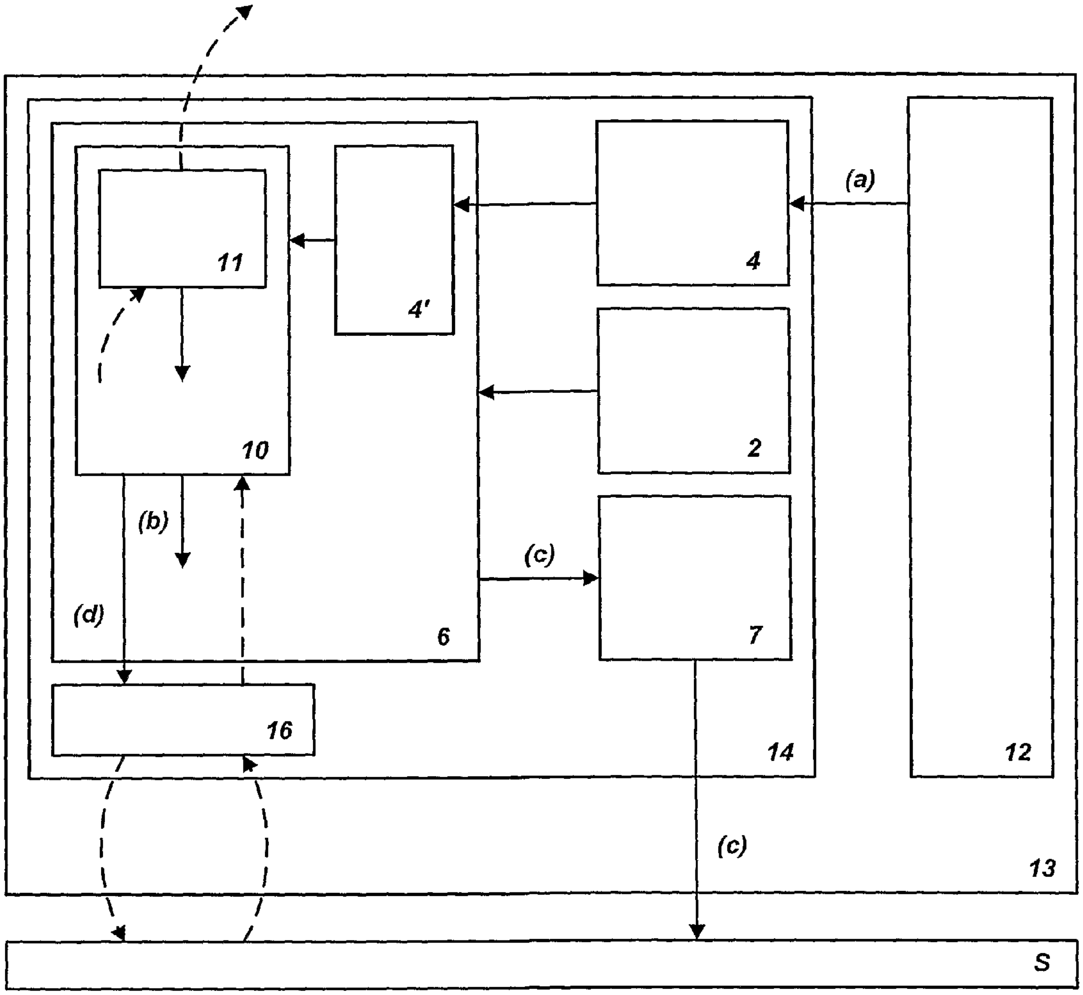
FIG. 12 is a schematic illustration of the embodiment of FIG. 11 comprising a biosensor or a nanochip.

In FIG. 12, the electric communication system further comprises at least a biosensor 16. It can be advantageous that the electric communication unit comprises a series of biosensor, which can be from the same or different types. Particularly, it can be preferable to measure two or more different parameters to confirm or to correlate a value of one parameter. The biosensor, which can also be a nanochip or the like is able to measure a biological, a chemical or a physical parameter, such as the dissolved oxygen in the blood through the skin, the pH of the skin, the protein level, the glucose level, the arterial pressure, enzymatic content, the resistance of the skin, the conductivity of the skin and the like. The biosensor can continuously measure the biological, the chemical or the physical parameters or it can measure them at predetermined intervals which are stored in the memory. The predetermined intervals can be for example 30 minutes or 1 hour after the time at which a series of pulses indicating that a medicine has to be taken was generated. This can be advantageous for having parameters representative of the effect of the medicine. Therefore, the processing unit will send a start signal (d) to the biosensor for activating it. The biosensor will measure the parameters. The processing unit will transmit the parameter data to the memory. The extraction of the parameter data can be done by a doctor, a nurse, the patient, by means of a portable computer, the base unit, a server of a network, and the like.

In a particular embodiment, the parameter stored in the memory can be used to generate an activation signal (b) resulting in a series of pulses (c) transmitted to the body contacts 7 to the skin (S). An example of such an application can be the measurement of the awake/sleeping condition of a driver of a car. In the case where the driver falls asleep at the wheel a series of pulses will alert and wake up the driver.

Figure 13:
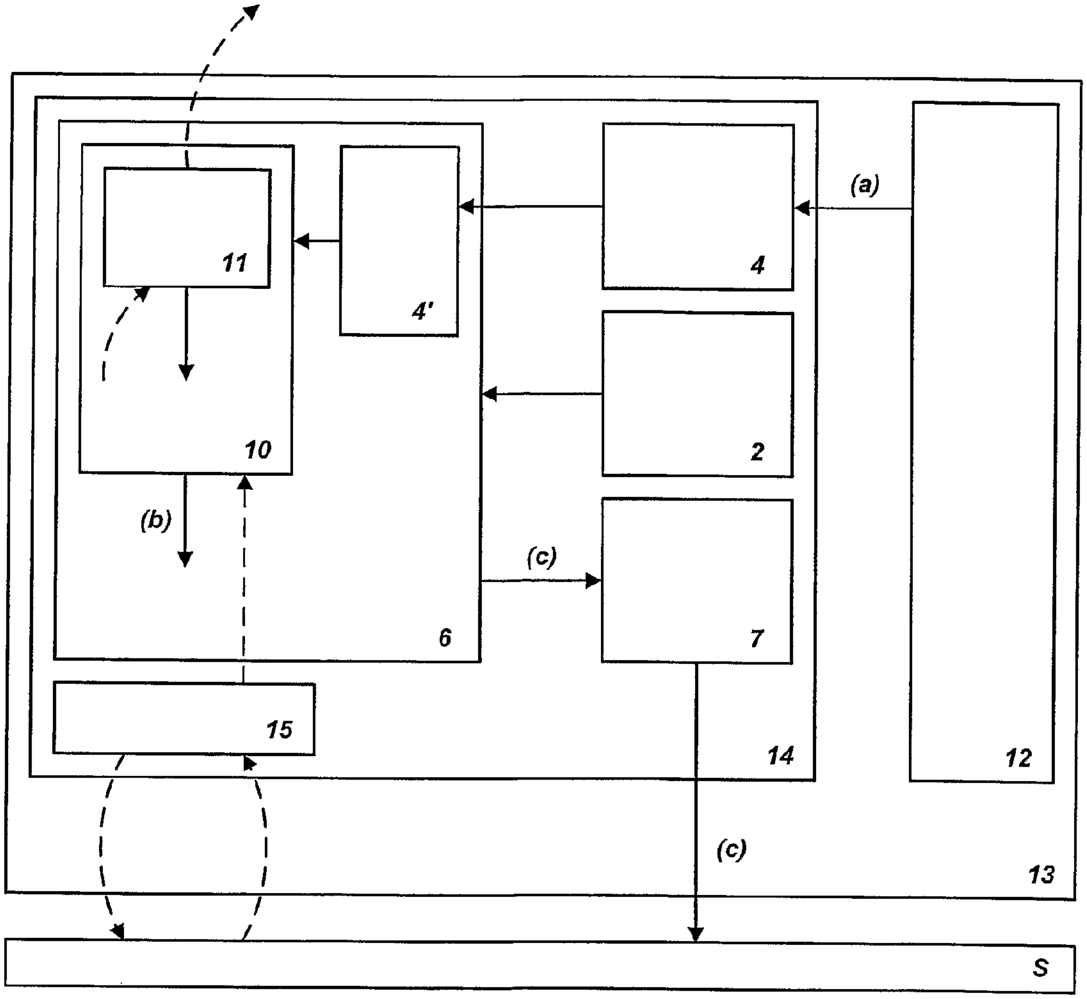
FIG. 13 is a schematic illustration of the embodiment of FIG. 11 comprising a recording means.

FIG. 13 illustrates an embodiment wherein the electric communication unit comprises at least a recording means 15. The recording means 15 is provided to transmit via the processing unit a confirmation data and to store it into the memory. The confirmation data concerns the time at which the series of pulses have effectively been generated and if the series of pulses has effectively been transmitted to the skin or even which series of pulses has been generated. The recording means is in fact every means able to detect a current flow, a current shape, a frequency of a signal, a pulse width, a pulse period, a pulse shape, a time, an interval of time and the like. Actually, every means suitable to store any data which can be useful to confirm that the series of pulses have effectively been generated, the time at which the series of pulses was generated, if the series of pulses has effectively been transmitted to the skin or even which series of pulses has been generated.

Other advantages of such an electric communication unit are given hereinafter. The electric communication unit is user friendly, the initialisation and the first use must be easy understandable for a normal adult person. The electric communication unit should have sufficient preservation. In particular, the preservation duration of the electric communication unit will preferably be function of the best before date of the medicine. The electric communication unit should also moreover be removable if desired. At the end of the user cycle, or at any other desired moment, the patch must be easily removable. Another property of the electric communication unit is that it should be durable in soapy water. For practical reasons soapy water should neither damage nor detach the unit from the skin. A further characteristic is that the electric communication unit will preferably be employable by an assistant taking the patient's place: An assistant can take a patient's place if this is preferable considering the circumstances. For example parents can apply it on their own body to administer their children's medicine correctly or geriatric helpers can use it instead of their elderly patients.

Moreover, the base unit can program several electric communication units with unique identifiers. These unique identifiers may be used by a central system which would store the data contained in several patches in a same hospital. For example, in the variant aforementioned, wherein each patient wears a patch comprising biosensors or nanochips to measure and to send values of biological, chemical or physical parameters to the processing unit, the electric communication unit can be provided to transmit the parameters in a wireless manner, for example in a RF manner or in a bluetooth manner to a central system or to the base unit. The parameters of each electric communication unit can be transmitted to a central system, without risks for confusion due to their unique identifiers. For example, if the parameters are transmitted to a central unit being accessible by a doctor, the doctor can check the compliance of the patient, verify the timely administration of the medicine or check the benefit of a particular treatment.

Moreover, the electric communication system can comprise a base unit, a central electric communication unit and secondary electric communication units. The base unit is for example provided to program the central electric communication unit according to the doctor's instructions in a department of an hospital. The central communication unit can be provided to generate several different series of pulses to a nurse wearing it, each patient corresponding to a particular series of pulses. Each secondary electric communication unit preferably comprises biosensors or nanochips to measure and to transmit biological, chemical or physical parameters to the processing unit. The electric communication unit can be provided to transmit them in a wireless manner, for example in a RF manner or in a bluetooth manner to a central system for the checking of the compliance of the patient, for the verification of the timely administration of the medicine or to check the benefit of a particular treatment.

The invention has been described here with a preferred use in the context of a medicine therapy. Of course, the invention can be used in a lot of different contexts, like, for reminding appointments, for awaking a mother just before feeding her baby, to avoid a driver to fall asleep, etc.

The invention claimed is:

1. A set comprising a medicine to be administered at predetermined points in time to a person and in combination therewith a reminding unit which is configured to be placed on said person's skin to remind the person at said predetermined points in time that said medicine is to be administered, which reminding unit comprises:

a support element (3), comprising:

a series of body contacts (7);

a pulse generator (6) connected to the series of body contacts (7), and provided for generating a series of non-therapeutic electric pulses (c) upon receipt of an activation signal (b) and for transmitting the series of non-therapeutic electric pulses (c) to the series of body contacts (7), the series of body contacts (7) being configured to transmit the series of non-therapeutic electric pulses (c) onto the skin of the person so that these electric pulses are felt by the person's skin; and a power supply (2) connected to the pulse generator (6), wherein said reminding unit is an adhesive patch comprising the support element (3) that has the series of body contacts (7), the pulse generator (6), and the power supply (2), wherein the adhesive patch comprises an adhesive layer (9) and a liner (8) stuck to said adhesive layer (9), wherein said adhesive patch is configured to be stuck onto the person's skin, the adhesive patch being formed as a thin flexible element, and said pulse generator (6) further comprises a processing unit (10) having a memory (11) wherein a data signal (a) comprising data indicative of said predetermined points in time at which said medicine should be administered to said person and the activation signal (b) should be generated is stored before the pulse generator (6) is put into operation, said processing unit (10) always generates and transmits the activation signal (b) at said points in time to said pulse generator (6), there is no physical user interface on said reminding unit to modify said points in time, and said pulse generator (6) comprising a power control arranged to put the pulse generator in operation at the moment of first use of the reminding unit when, after removal of the liner (8) from the adhesive layer (9), the adhesive patch is stuck onto the person's skin to generate, upon receipt of said activation signal, said series of non-therapeutic electric pulses.

2. A set comprising a medicine and a reminding unit as claimed in claim 1, wherein said medicine is contained in a packaging which also contains said reminding unit.

3. A set comprising a medicine and a reminding unit as claimed in claim 1 or 2, wherein said reminding unit is disposable.

4. A set comprising a medicine and a reminding unit as claimed in claim 1, wherein said reminding unit is enclosed in a packaging and wherein said reminding unit is part of a reminding system which comprises said reminding unit and a base unit, wherein said reminding unit comprises a receiver and wherein said base unit is a wireless transmitter to transmit the data signal to the receiver of said reminding unit without opening said packaging.

5. A set comprising a medicine and a reminding unit as claimed in claim 1, wherein said pulse generator (6) comprises a current source for generating said series of pulses having an intensity ranging from 10 mAdc to 50 mAdc.

6. A set comprising a medicine and a reminding unit as claimed in claim 1, wherein the pulses have a width comprised between 10 μs and 1 ms.

7. A set comprising a medicine and a reminding unit as claimed in claim 1, wherein the pulses are separated by a period of 100 μs to 100 ms.

8. A set comprising a medicine and a reminding unit as claimed in claim 1, wherein the series of pulses further comprises a plurality of bursts, each burst comprising a set of pulses, the bursts being separated from each other by a period of time without pulses.

9. A set comprising a medicine and a reminding unit as claimed in claim 1, wherein the pulse generator (6) comprises a power control provided to trigger the pulse generator (6) in operation when a small leakage current is caused at said moment of first use.

10. A set comprising a medicine and a reminding unit as claimed in claim 1, wherein said pulse generator (6) is configured to be put in operation at the moment of first application of the reminding unit onto the person's skin.

11. A set comprising a medicine and a reminding unit as claimed in claim 1, wherein said medicine is contained in transdermal patches which are configured to be placed at said predetermined points in time on the person's skin to administer the medicine to that person.

12. A set comprising a transdermal patch, and in combination therewith a separate reminding unit, for use in a medicine therapy wherein transdermal patches are used which are configured to be removed or replaced at predetermined points in time from a person's skin, which transdermal patch is configured to be placed on the person's skin to deliver a drug to that person and which is to be removed or replaced at one of said predetermined points in time from that person's skin, and said separate reminding unit being configured to be placed on said person's skin to remind the person at said predetermined point in time that the transdermal patch has to be removed or replaced, which reminding unit comprises:

- a support element (3), comprising:
  - a series of body contacts (7);
  - a pulse generator (6) connected to the series of body contacts (7), and provided for generating a series of non-therapeutic electric pulses (c) upon receipt of an activation signal (b) and for transmitting the series of non-therapeutic electric pulses (c) to the series of body contacts (7), the series of body contacts (7) being configured to transmit the series of non-therapeutic electric pulses (c) onto the skin of the person so that these electric pulses are felt by the person's skin; and
  - a power supply (2) connected to the pulse generator (6),
  - wherein said reminding unit is an adhesive patch comprising the support element (3) that has the series of body contacts (7), the pulse generator (6), and the power supply (2), wherein the adhesive patch comprises an adhesive layer (9) and a liner (8) stuck to said adhesive layer (9), wherein said adhesive patch is configured to be stuck onto the person's skin, the adhesive patch being formed as a thin flexible element, and said pulse generator (6) further comprises a processing unit (10) having a memory (11) wherein a data signal (a) comprising data indicative of said predetermined point in time at which said transdermal patch has to be removed or replaced and the activation signal (b) should be generated is stored before the pulse generator (6) is put in operation,
- said processing unit (10) being provided to generate and transmit the activation signal (b) at said point in time to said pulse generator (6),
- there is no physical user interface on said reminding unit to modify said point in time, and
- said pulse generator (6) comprising a power control arranged to put the pulse generator in operation at the moment of first use of the reminding unit when, after removal of the liner (8) from the adhesive layer (9), the adhesive patch is stuck onto the person's skin to generate, upon receipt of said activation signal, said series of non-therapeutic electric pulses.

13. A set comprising a transdermal patch and in combination therewith a separate reminding unit as claimed in claim 12, wherein said transdermal patch is contained in a packaging which also contains said reminding unit.

14. A set comprising a transdermal patch and in combination therewith a separate reminding unit as claimed in claim 12, wherein said reminding unit is disposable.

15. A set comprising a transdermal patch and in combination therewith a separate reminding unit as claimed in claim 12, wherein said pulse generator (6) comprises a current source for generating said series of pulses having an intensity ranging from 10 mAdc to 50 mAdc.

16. A set comprising a transdermal patch and in combination therewith a separate reminding unit as claimed in claim 12, wherein the pulses have a width comprised between 10 μs and 1 ms.

17. A set comprising a transdermal patch and in combination therewith a separate reminding unit as claimed in claim 12, wherein the pulses are separated by a period of 100 μs to 100 ms.

18. A set comprising a transdermal patch and in combination therewith a separate reminding unit as claimed in claim 12, wherein the series of pulses further comprises a plurality of bursts, each burst comprising a set of pulses, the bursts being separated from each other by a period of time without pulses.

19. A set comprising a transdermal patch and in combination therewith a separate reminding unit as claimed in claim 12, wherein the pulse generator (6) comprises a power control provided to trigger the pulse generator (6) in operation when a small leakage current is caused at said moment of first use.

20. A set comprising a transdermal patch and in combination therewith a separate reminding unit as claimed in claim 12, wherein said pulse generator (6) is configured to be put in operation at the moment of first application of the reminding unit onto the person's skin.

21. A medicine packaging containing a number of transdermal patches which are provided to be used in a medicine therapy wherein the transdermal patches are configured to be removed or replaced at predetermined points in time from a person's skin, which transdermal patches are each configured to be stuck onto said person's skin to deliver a drug to that person, and each transdermal patch comprises a reminding unit which is configured to remind the person at the predetermined point in time at which the transdermal patch has to be removed or replaced and further an adhesive layer (9), a liner (8) stuck to said adhesive layer (9), and said drug which is to be delivered transdermally, said reminding unit comprising:

- a support element (3), comprising:
  - a series of body contacts (7);
  - a pulse generator (6) connected to the series of body contacts (7), and provided for generating a series of non-therapeutic electric pulses (c) upon receipt of an activation signal (b) and for transmitting the series of non-therapeutic electric pulses (c) to the series of body contacts (7), the series of body contacts (7) being configured to transmit the series of non-therapeutic electric pulses (c) onto the skin of the person so that these electric pulses are felt by the person's skin; and
  - a power supply (2) connected to the pulse generator (6),
  - wherein said pulse generator (6) further comprises a processing unit (10) having a memory (11) wherein a data signal (a) comprising data indicative of said predetermined point in time at which the transdermal patch has to be removed or replaced and the activation signal (b) should be generated is stored before the pulse generator (6) is put in operation, said processing unit (10) being provided to generate and transmit the activation signal (b) at said point in time to said pulse generator (6), there is no physical user interface on said reminding unit to modify said point in time, and said pulse generator (6) comprising a power control arranged to put the pulse generator in operation at the moment of first use of the reminding unit when, after removal of the liner (8) from the adhesive layer (9), the transdermal patch is stuck onto the person's skin to generate, upon receipt of said activation signal, said series of non-therapeutic electric pulses.

22. A medicine packaging containing a number of transdermal patches as claimed in claim 21, wherein said pulse generator (6) comprises a current source for generating said series of pulses having an intensity ranging from 10 mAdc to 50 mAdc.

23. A medicine packaging containing a number of transdermal patches as claimed in claim 21, wherein the pulses have a width comprised between 10 μs and 1 ms.

24. A medicine packaging containing a number of transdermal patches as claimed in claim 21, wherein the pulses are separated by a period of 100 μs to 100 ms.

25. A medicine packaging containing a number of transdermal patches as claimed in claim 21, wherein the series of pulses further comprises a plurality of bursts, each burst comprising a set of pulses, the bursts being separated from each other by a period of time without pulses.

26. A medicine packaging containing a number of transdermal patches as claimed in claim 21, wherein the pulse generator (6) comprises a power control provided to trigger the pulse generator (6) in operation when a small leakage current is caused at said moment of first use.

27. A medicine packaging containing a number of transdermal patches as claimed in claim 21, wherein said pulse generator (6) is configured to be put in operation at the moment of first application of the reminding unit onto the person's skin.

* * * * *